United States Patent
Kok et al.

(10) Patent No.: US 7,545,487 B2
(45) Date of Patent: Jun. 9, 2009

(54) INSPECTION OF EGGS IN THE PRESENCE OF BLOOD

(75) Inventors: Hugo L. Kok, Nijmegen (NL); Jan Hordijk, Aalten (NL)

(73) Assignee: Staalkat International B.V., Aalten (NL)

( * ) Notice: Subject to any disclaimer, the term of this patent is extended or adjusted under 35 U.S.C. 154(b) by 0 days.

(21) Appl. No.: 11/575,125

(22) PCT Filed: Sep. 5, 2005

(86) PCT No.: PCT/NL2005/000639

§ 371 (c)(1),
(2), (4) Date: Apr. 22, 2008

(87) PCT Pub. No.: WO2006/031100

PCT Pub. Date: Mar. 23, 2006

(65) Prior Publication Data

US 2008/0252877 A1   Oct. 16, 2008

(30) Foreign Application Priority Data

Sep. 14, 2004   (NL) .................................. 1027042

(51) Int. Cl.
*A01K 43/00* (2006.01)
*G01N 33/08* (2006.01)

(52) U.S. Cl. .......................................... 356/53; 356/52

(58) Field of Classification Search ........................ None
See application file for complete search history.

(56) References Cited

U.S. PATENT DOCUMENTS 3,004,664 A   10/1961   Dreyfus
3,255,660 A   6/1966   Hiri
4,063,822 A   12/1977   deJong et al.
6,504,603 B1 *   1/2003   Schouenborg ................ 356/53
6,750,954 B2 *   6/2004   Hebrank et al. ................ 356/53

FOREIGN PATENT DOCUMENTS

| EP | 1074831 A1 | 2/2001 |
| JP | 06043093 A | 2/1994 |
| JP | 10115583 A | 5/1998 |
| JP | 2001041882 A | 2/2001 |
| JP | 2003065961 A | 3/2003 |
| JP | 2004-347327 A | 12/2004 |

\* cited by examiner

*Primary Examiner*—Michael P Stafira
(74) *Attorney, Agent, or Firm*—Townsend and Townsend and Crew LLP

(57) ABSTRACT

The invention relates to a device for inspecting eggs for the presence of blood. The device comprises a light source in order to pass light at a first wavelength which is not selectively absorbed by blood and light at a second wavelength which is selectively absorbed by blood through an egg to be inspected. Furthermore, the device comprises detection means for converting the light transmission through the egg to be inspected for each of the two wavelengths into corresponding signals, each of the said signals being representative of the light transmission at the relevant wavelength. The device also comprises signal-processing means which are transmission associated with the first wavelength and the light transmission associated with the second wavelength based on the signals emanating from the detection means and to emit a decision signal which is representative of the decision whether or not an egg contains blood on the basis of this ratio. According to the invention, the light source comprises one or more identical LED's (Light Emitting Diode) for generating light which passes through the egg. In use the one or more LED's emit light within a certain narrow spectrum, which spectrum comprises both the first and the second wavelength.

25 Claims, 3 Drawing Sheets

INSPECTION OF EGGS IN THE PRESENCE OF BLOOD

CROSS-REFERENCES TO RELATED APPLICATIONS

This application is a National Stage of International Application No. PCT/NL2005/000639, filed Sep. 5, 2005, and which claims the benefit of Netherlands Patent App. No. 1027042, filed Sep. 14, 2004. The disclosures of the above applications are incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The invention relates to a device for inspecting eggs for the presence of blood. The device comprises a light source in order to pass light of a first wavelength, which is not selectively absorbed by blood, and light of a second wavelength, which is selectively absorbed by blood, through an egg to be inspected. The device further comprises detection means for converting the light transmission through the egg to be inspected for each of the two wavelengths into corresponding signals, each of the said signals being representative of the light transmission at the relevant wavelength. Furthermore the device comprises signal-processing means which are designed to determine the ratio between the light transmission associated with the first wavelength and the light transmission associated with the second wavelength based on the signals emanating from the detection means and to emit a decision signal which is representative of the decision whether or not an egg contains blood on the basis of this ratio.

A device of this type is known from NL 7504011. The light transmission is the light energy which is transmitted through the egg at the two wavelengths. With eggs that do not contain blood, the ratio of the measurements of the transmitted light energy at the two different wavelengths is virtually fixed. With eggs that do contain blood, the light of the second wavelength is absorbed more than the light of the first wavelength as a result of the presence of blood in the egg, which disturbs the ratio between the transmitted light energy at the two wavelengths. This disturbance is converted by the device into a decision signal which indicates that the egg contains blood and therefore has to be rejected. With the known device, different light sources are used for the light of the first wavelength and of the second wavelength. In particular, for the first wavelength, a halogen lamp with an interference filter is used in the known device. For the second wavelength, a mercury spectral lamp with an interference filter is used. The known device further comprises what is known as a rotating butterfly which covers either both or one of the two light sources alternatively, as a result of which alternately a light beam from the one and from the other light source hits the egg. When the butterfly covers both lamps, no light falls on the detection means and what is known as a zero measurement can be carried out in order to compensate for the offset of the detection means.

BRIEF SUMMARY OF THE INVENTION

It is an object of the invention to provide an improved device for inspecting eggs for the presence of blood.

This object is achieved by a device for inspecting eggs for the presence of blood, comprising:
  a light source in order to pass light of a first wavelength which is not selectively absorbed by blood and light of a second wavelength which is selectively absorbed by blood through an egg to be inspected,
  detection means for converting the light transmission through the egg to be inspected for each of the two wavelengths into corresponding signals, each of the said signals being representative of the light transmission at the relevant wavelength,
  signal-processing means which are designed to determine the ratio between the light transmission associated with the first wavelength and the light transmission associated with the second wavelength based on the signals emanating from the detection means and to emit a decision signal which is representative of the decision whether or not an egg contains blood on the basis of this ratio, wherein the light source comprises one or more identical LED's (Light Emitting Diode) for generating the light which passes through the egg, wherein the one or more identical LED's in use emit light within a certain narrow spectrum, which spectrum comprises both the first and the second wavelength.

In an advantageous preferred embodiment, one or more identical LED's are used which in use emit amber light in a spectrum from 550-620 nm, which spectrum comprises both the first and the second wavelength, which are preferably approximately 600 nm and approximately 577 nm, respectively. This offers the advantage that light of a high intensity is generated in the spectrum relevant to the application of detecting blood in eggs and, in other words, only little light which is not useful for the light transmission measurements through the eggs at the two wavelengths is generated.

In one preferred embodiment, the detection means comprise a first sensor with a first filter placed in front thereof, which selectively allows to pass light at the first wavelength, and a second sensor with a second filter placed in front thereof, which selectively allows to pass light at the second wavelength. With this preferred embodiment, the first sensor, for example a photodiode, is used to convert the light transmission at the first wavelength into a corresponding first signal. The second sensor, for example a photodiode, is used to convert the light transmission at the second wavelength into a corresponding second signal. The filters placed in front of the sensors are preferably designed as interference filters and block light transmitted through the egg, except at the two respective wavelengths.

Preferably, the detection means comprise a semitransparent mirror, which semitransparent mirror deflects part of the light transmitted through the egg to one of the sensors and allows to pass part of the light to the other sensor. It is important for good detection of blood that the transmission measurement is based on one light beam transmitted through the egg. By using the semitransparent mirror, light from one beam can be passed to the two sensors in a simple manner.

In an alternative embodiment, the detection means comprise a dichromatic mirror which acts as a mirror for the one wavelength and allows light at the other wavelength to pass through, as a result of which light from one beam can easily be transmitted to the two sensors.

One of the properties of an LED is that the emitted light intensity within the emitted spectrum is dependent on the temperature. As a result of the shift in the spectrum of emitted light when the temperature of the LED changes, a change occurs in the ratio between the first and second signal and eggs which are fine per se could be seen as eggs containing blood or vice versa. In a particularly advantageous preferred embodiment of the invention, the signal-processing means are designed to detect a variation in the ratio between the light transmission associated with the first wavelength and the light transmission associated with the second wavelength during the inspection of a plurality of eggs in succession and to correct the effect of the variation in the ratio on the decision whether or not an egg contains blood. Due to this measure, it is possible to continually correct the measurements based on the passing batch of eggs and to eliminate the effect of the spectrum shift of the light emitted by the LED on the assessment of the eggs.

The invention furthermore relates to a method for inspecting eggs for the presence of blood, wherein
light is transmitted through an egg to be inspected by means of an LED, which light comprises a first wavelength which is not selectively absorbed by blood and comprises a second wavelength which is selectively absorbed by blood,
the light transmission through the egg to be inspected at the two wavelengths is converted into corresponding signals, said signals each being representative of the light transmission at the wavelength concerned,
based on the signals, the ratio is determined between the light transmission associated with the first wavelength and the light transmission associated with the second wavelength and it is decided on the basis of this ratio whether or not an egg contains blood.

Further features and advantages of the invention will emerge in the following description of a preferred embodiment with reference to the attached drawing.

DETAILED DESCRIPTION OF THE INVENTION

Figure 1:
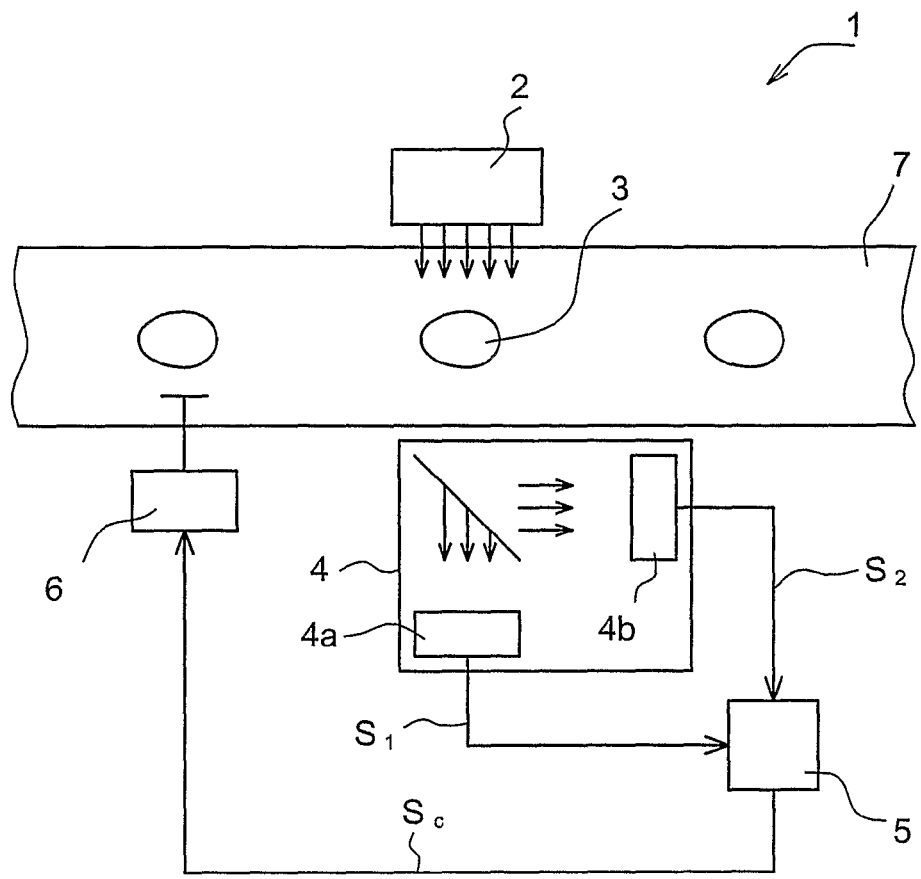
FIG. 1 diagrammatically shows a preferred embodiment of a device for inspecting eggs for blood according to the invention.

FIG. 1 shows a device for inspecting eggs denoted by reference numeral 1. The device 1 comprises an LED 2 (Light Emitting Diode) which serves as a source of light in order to transmit light through an egg 3 placed in front of it. It is also possible to use a group of several LEDs instead of one LED. The eggs are conveyed past the LED 2 one by one by means of a conveyor belt 7 or the like. Detection means 4 have been placed opposite the LED 2, on the other side of the path of the egg 3.

In the embodiment shown, the detection means 4 comprise optical sensors 4a and 4b which are each sensitive to light of a specific wavelength $\lambda 1$ and $\lambda 2$, respectively. Light of a first wavelength $\lambda 1$ is not selectively absorbed by blood, light of the second wavelength $\lambda 2$ is. The light emitted by the LED 2 which shines through the egg 3 to be inspected is received by the sensors 4a and 4b and converted into a first signal S1 and a second signal S2 respectively which are representative of the light transmission of the light at the two wavelengths $\lambda 1$ and $\lambda 2$, respectively, through the egg.

The signals S1 and S2 are supplied to a signal-processing unit 5 which, based on the signals S1 and S2 originating from the sensors 4a and 4b, determines the ratio between the light transmission through the egg 3 associated with the first wavelength $\lambda 1$ and the light transmission through the egg 3 associated with the second wavelength $\lambda 2$. Based on this ratio between the light transmissions, the signal-processing unit generates a decision signal which is representative of the decision whether or not an egg 3 contains blood. When it is decided that the egg 3 does contain blood, the signal-processing unit 5 feeds a control signal Sc to an ejector unit 6 which removes an egg from the row on the conveyor belt 7. As an alternative to the ejector unit 6, it is also possible to feed a control signal to a multi-track egg-sorting machine (not shown), as a result of which eggs containing blood are fed to a track of the sorting machine intended for this purpose and are discharged. The decision whether or not an egg contains blood is taken by comparing the ratio between the light transmission at a first wavelength and the light transmission at a second wavelength to a threshold value. If the ratio exceeds the threshold value, the decision is made that an egg contains blood.

In a first illustrated preferred embodiment of the invention, the signal-processing unit 5 (cf. FIG. 3) comprises an amplifier 8 with an amplification factor V1 which is kept at a constant value and an adjustable amplifier 9 with an amplification factor V2 for respectively amplifying the signals originating from the sensors 4a and 4b in such a manner that, after the amplified signals are fed to a division component 11, a ratio $(S1*V1)/(S2*V2)$ is obtained which is equal to a predetermined constant, preferably equal to one.

With this design of the signal-processing unit 5, it is for example possible to set the device as follows: initially, a first egg 3 is placed between the LED 2 and the detection means 4 and the amplification factors are adjusted in such a manner that a ratio of $(S1*V1)/(S2*V2)$ equals one is obtained. Subsequently, the next egg 3 is placed between the LED 2 and the detection means 4. If the signal S2 associated with the second wavelength $\lambda 2$ is weaker than with the first egg 3, the amplification V2 is adjusted so that a ratio equal to one is obtained again. If the signal S2 is stronger than with the first egg 3, the amplification factor V2 is left as it is. These steps are repeated with a group of for example thirty to one hundred eggs. Using this setting method, the signal-processing unit is adjusted to an egg 3 with a relatively strong light absorption at $\lambda 2$.

In a further preferred embodiment (see FIG. 3), an electronic component 10, preferably a microprocessor, is used for generating the control signal Sc for the ejector unit 6. Furthermore, the electronic component 10 may be used for continually adjusting the amplification factor V2 of the amplifier 9. Setting could be effected automatically using a microprocessor. It is also possible to incorporate the components 10 and 11 into one microprocessor.

Figure 4:
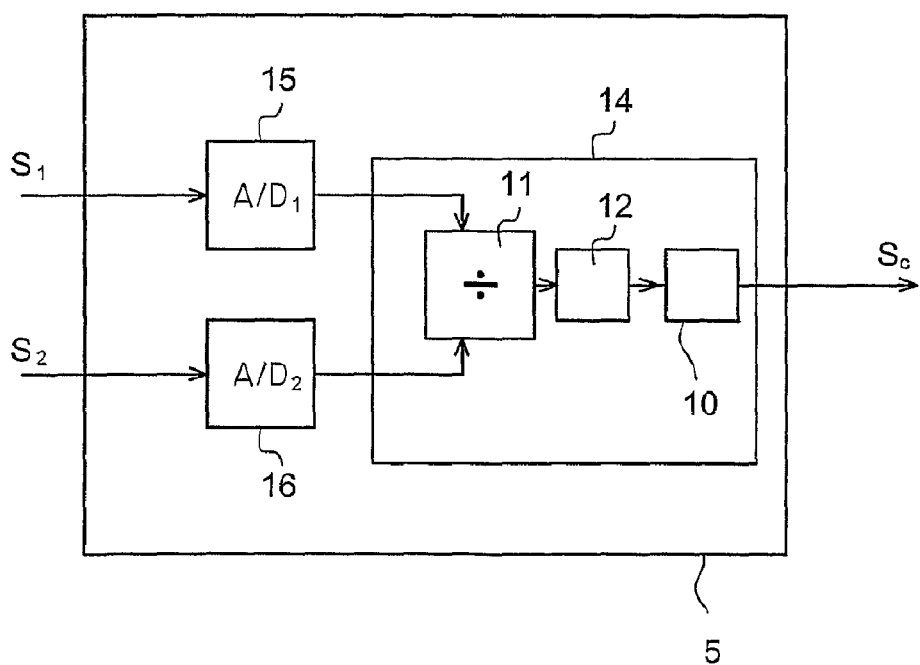

In an alternative advantageous preferred embodiment (see FIG. 4), the signal-processing unit 5 comprises two A/D converters 15, 16 for converting the signals S1 and S2 into digital signals. Furthermore, the signal-processing unit 5 comprises a component 11 for determining the ratio of the signals S1 and S2. The ratio S1/S2 is supplied to a monitoring component 12 which calculates an average value for the ratio S1/S2 in each case based on a specific number of eggs. Using the average values obtained in each case, the course of the ratio S1/S2 is monitored and when the average of the ratio S1/S2 deviates too much, the ratio S1/S2 is multiplied by a correction factor with which the variation in the ratio S1/S2 can be compensated for. The signal from component 12 is supplied to a component 10 which generates the decision signal and sends a control signal Sc to the ejector unit 6. Preferably, the components 10, 11 and 12 are incorporated in a microprocessor 14, as shown in FIG. 4.

Above, a preferred embodiment is described in which the ratio S1/S2 is monitored by means of an average value of said ratio. However, it is not imperative to use the average in order to monitor the ratio S1/S2. The ratio S1/S2 can also be monitored using another suitable statistically determined value, such as a median for example.

The above described signal-processing units have a specific advantage when they are being used with an LED:

An LED has the characteristic that the light intensity it emits within the emitted spectrum is temperate dependent. A change in temperature of the LED results in a change in the ratio between the first signal S1 and the second signal S2 due to the shift in the light intensity within the spectrum of the emitted light, which could possibly lead to eggs 3 which are fine per se being seen as eggs containing blood or vice versa. It is possible to compensate for the shift of the spectrum by measuring the temperature of the LED and using a temperature-dependent correction factor. However, a temperature measurement requires additional measuring means, making the device more complex and more expensive.

Figure 3:
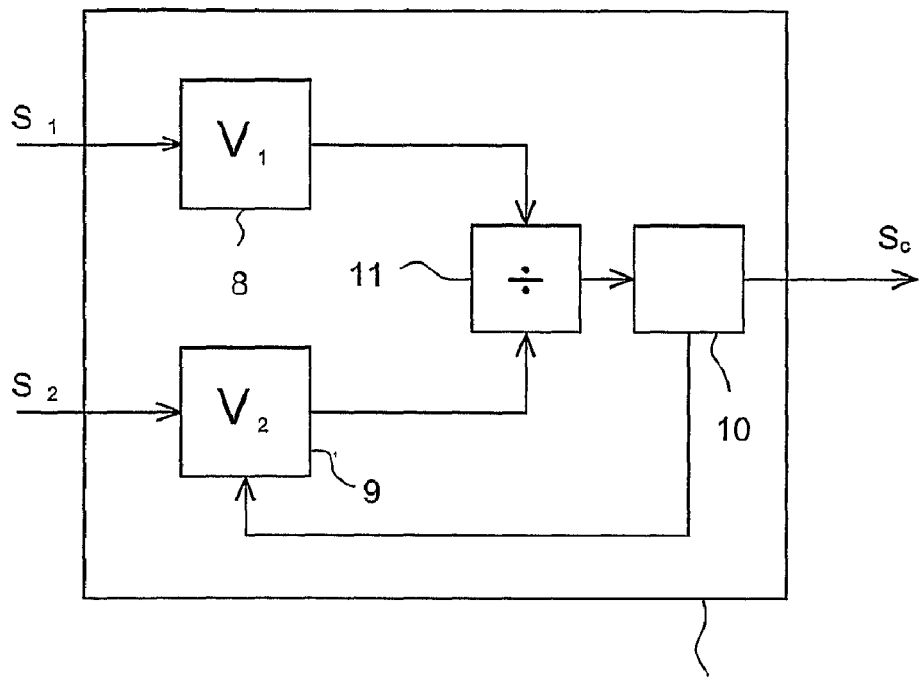

With the embodiment shown in FIG. 3, it is more advantageous if the microprocessor 10 adjusts the amplification continuously based on the transmission measurements which are already being carried out anyway. The device is then constantly calibrated in terms of its amplification, based on a group of eggs 3 which are conveyed past the device 1 at the relevant point in time. In this case, the group of eggs 3 may be a group of thirty to one hundred eggs. Constantly matching the amplification to the passing batch of eggs prevents eggs 3 from being wrongly rejected.

It is most advantageous to use the embodiment of the signal-processing unit 5 shown in FIG. 4, in which the ratio S1/S2 is monitored, and to apply the correction factor when a variation in the ratio S1/S2 is detected as a result of a shift in the spectrum of the LED 2. As a result, it is possible to eliminate the effect of the spectrum shift of the LED 2 on the decision whether or not an egg contains blood. In practice, the average value of the ratio S1/S2 is determined for a group of in each case approximately 30-100 eggs. When it is detected that the average is starting to move, a correction factor can be applied. The reciprocal of the average value which has just been determined could be used as a correction factor, for example. Continually adjusting the correction to the passing batch of eggs prevents eggs from being wrongly rejected. Preferably, the extreme values of the ratio S1/S2 within the group are removed when determining the average of the ratio S1/S2 in order to eliminate the effect of any eggs containing blood on the correction.

Incidentally, it is not necessary for the average of the ratio between the light transmission at the first wavelength and the light transmission at the second wavelength to be corrected in order to correct for the variation in said ratio. A method in which the threshold value is corrected when said ratio varies is also conceivable.

The light transmission at the relevant spectrum concerned is also affected by the colour of the egg, white or brown. With a known inspection device according to U.S. Pat. No. 6,504,603, the colour is determined for each egg individually. Thus, it is known whether blood detection is taking place on a white or brown egg, so that the measurement can be corrected for a brown egg. Continually adjusting the amplification of the signals or of the correction factor in order to overcome the temperature dependence of the LED, as explained above with reference to FIGS. 3 and 4, has the additional advantage that the problem of batches of differently coloured eggs is eliminated and a correction for each individual egg as is carried out in U.S. Pat. No. 6,504,603 is not required.

The adaptive nature of the signal-processing unit 5 can also advantageously be used in an inspection device with a light source other than LED. The signal-processing unit 5 will also automatically adjust when a batch of white eggs is inspected first followed by a batch of brown eggs.

Inspection devices for eggs with the use of light that is generated by LED's is as such known from the prior art. However, with those light is generated by different LED's which each emit different wavelengths. In e.g. JP 2001041882 a device is disclosed with different groups of LED's that each generate light with a different wavelength.

From JP 2003065961 an inspection device for eggs is known in which two different light emitting elements are applied that each generate light with a different wavelength.

However, according to the invention the LED 2 generates light within a narrow spectrum which comprises the first and second wavelengths $\lambda 1$ and $\lambda 2$, respectively.

Preferably, an LED is used which generates amber light in a spectrum from 550-620 nm, the wavelengths $\lambda 1$ and $\lambda 2$ preferably being approximately 600 nm and approximately 577 nm, respectively. This offers the advantage that light of a high intensity is generated in the relevant spectrum. This offers an advantage over light sources known from the prior art for inspecting eggs for blood, such as for example halogen or xenon lamps. These lamps generate light with a very wide spectrum, while in order to measure the light transmission through an egg 3 only light of the two wavelengths $\lambda 1$, $\lambda 2$ which are within a specific limited bandwidth is needed. With the known devices, the wide spectrum of the halogen and xenon lamps is attenuated by using interference filters. Nevertheless, this light impinges on the detection means over a wide spectrum in attenuated fashion and makes a significant contribution to the measurement of the light transmission and thus disturbs the measurement result. By now using an LED 2 with a limited spectrum, little light is generated which is not useful for the light transmission measurements through the eggs 3 at the two wavelengths $\lambda 1$, $\lambda 2$.

By switching the LED 2 on and off, in each case one light pulse is emitted. When the LED 2 is switched off, a zero measurement is preferably carried out each time in order to compensate for the offset of the detection means 4. Because the LED 2 emits light pulses, no mechanical component is required in order to cover the light source 2 or the detection means 4 for a zero measurement.

Flash lamps are known per se from the prior art, such as for example xenon flash lamps, which make a mechanical butterfly, such as disclosed in NL 7504011, obsolete. However, flash lamps of this type are often expensive and only have a limited service life. The known flash lamps can only generate a very short light pulse, for example of 0.1 ms or less. One disadvantage of a very short light pulse is that a high-frequency signal is generated during the measurements of the light transmission through the eggs. The noise which affects the measurements generally has a large high-frequency component. In order nevertheless to obtain a good signal/noise ratio, which is important since the signals measured are very weak due to the fact that only little light is transmitted through an egg, it is necessary to use a high light intensity if the light pulses are very short. This in turn has an adverse effect on the service life of the flash lamp.

By means of the LED 2 light pulses of arbitrary duration can be generated, for example 10 ms. As a result, a relatively low-frequency signal is generated compared to the use of the known flash lamps, making it possible to reduce the effect of high-frequency noise disturbances on the light transmission measurements by filtering with a low-pass filter. This makes use of light of a much lower intensity possible, which leads to a saving of energy and increases the service life of the light source. Furthermore, compared to a flash lamp, an LED has the advantage that it only requires a low electrical voltage, which is considerably safer than the high voltage required when using a flash lamp. In addition, when a service engineer wants to check the operation of the inspection device, an LED does not blind whereas a flash lamp does and can severely hamper him in his work in practice.

Figure 2:
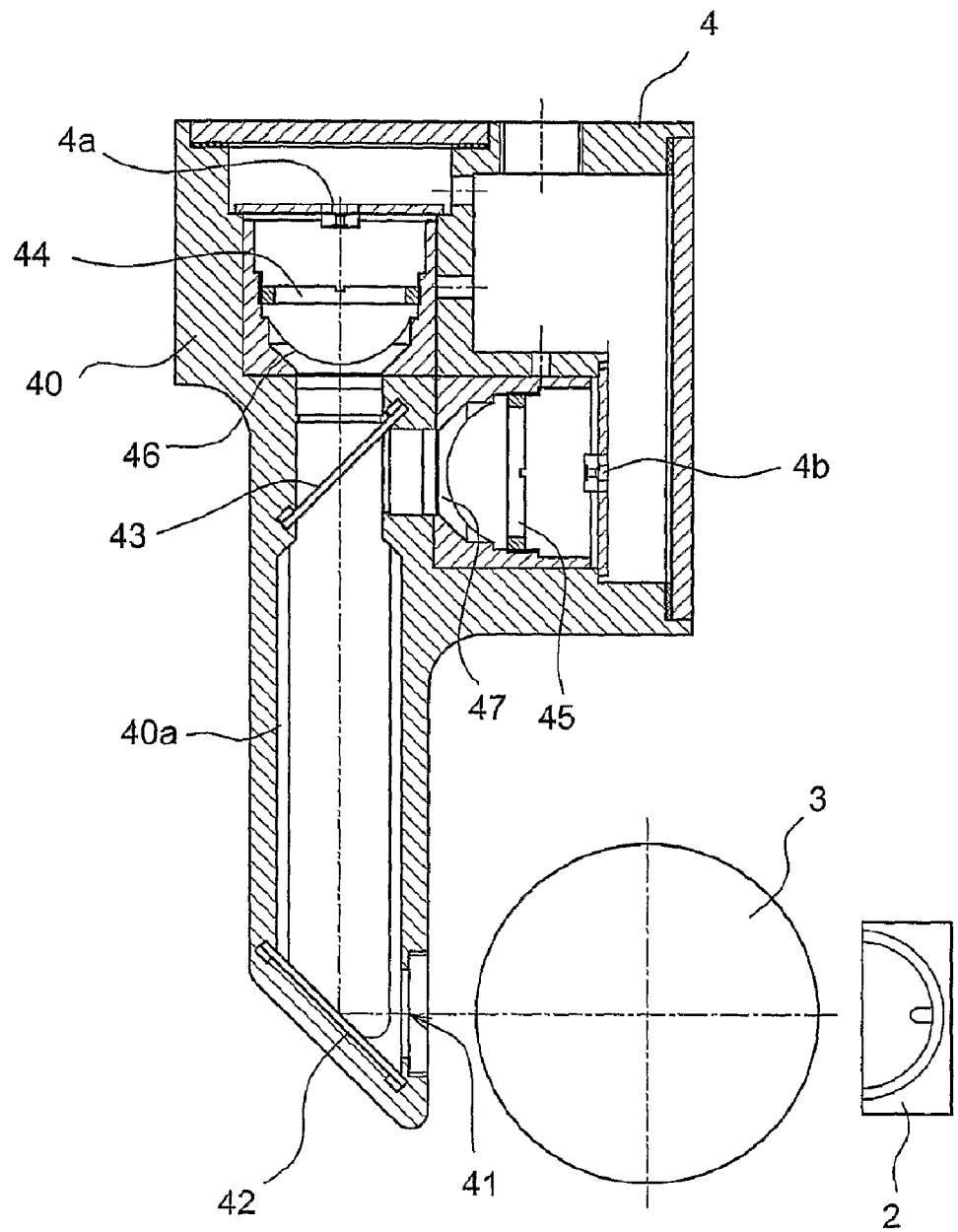
FIG. 2 shows a part of a preferred embodiment of the device from FIG. 1, FIG. 3 diagrammatically shows an embodiment of a signal-processing unit for the device from FIG. 1, and FIG. 4 diagrammatically shows another embodiment of a signal-processing unit for the device from FIG. 1.

FIG. 2 shows a part of the inspection device of FIG. 1 in more detail. Reference numeral 2 again denotes the LED. The LED 2 preferably comprises a fitted optical element in order to be able to focus a narrow light beam onto the egg 3.

Furthermore, FIG. 2 shows the detection means 4 which comprise a housing 40. The light transmitted through the egg 3 enters via an aperture 41 in the housing 40 and impinges on a mirror 42 which is positioned at an angle to the light beam, preferably at an angle of 45°. The light beam is directed to a subsequent mirror 43 by a tubular section 40a of the housing 40. The second mirror 43 is designed as a semitransparent mirror so that part of the light beam is reflected and part is allowed to pass. The mirror 43 is positioned at an angle, preferably at an angle of 45°, relative to the light beam in the housing part 40a. The light transmitted through the mirror 43 impinges on the first sensor 4a, the reflected and therefore deflected light impinges on the second sensor 4b. The tubular section 40a of the housing 40 and the two mirrors 42 and 43 located therein ensure that as little scattered light as possible, which enters via the aperture 41, reaches the sensors 4a and 4b and thereby disturbs the measurement of the light transmission.

The sensors 4a and 4b are preferably designed as a photodiode. A lens 46 is placed in front of the first sensor 4a which focuses the beam of light onto the sensor 4a. Furthermore, an interference filter 44 is placed in front of the sensor 4a, which interference filter 44 lets through light of the first wavelength $\lambda 1$, i.e. approximately 600 nm. A lens 47 is placed in front of the second sensor 4b, which lens 47 focuses the beam of light onto the sensor 4b. Furthermore, a second interference filter 45 is placed in front of the second sensor 4b, which second interference filter 45 lets through light of the second wavelength $\lambda 1$, i.e. of approximately 577 nm.

It will be clear the detection means may also be of a different design to that described above with reference to FIG. 2. Thus, for example, a dichromatic mirror can be used instead of a semitransparent mirror, which dichromatic mirror lets through light of the first wavelength $\lambda 1$ and reflects light of the second wavelength $\lambda 2$. It is also possible to use other suitable sensors and filters in a different arrangement with respect to each other without departing from the inventive idea.

The invention claimed is:

1. A device for inspecting eggs for the presence of blood, comprising:
    a light source in order to pass light of a first wavelength which is not selectively absorbed by blood and light of a second wavelength which is selectively absorbed by blood through an egg to be inspected,
    detection means for converting the light transmission through the egg to be inspected for each of the two wavelengths into corresponding signals, each of the said signals being representative of the light transmission at the relevant wavelength,
    signal-processing means which are designed to determine the ratio between the light transmission associated with the first wavelength and the light transmission associated with the second wavelength based on the signals emanating from the detection means and to emit a decision signal which is representative of the decision whether or not an egg contains blood on the basis of this ratio,
    wherein the light source comprises one or more identical LED's (Light Emitting Diode) for generating the light which passes through the egg, wherein the one or more identical LED's in use emit light within a certain narrow spectrum, which spectrum comprises both the first and the second wavelength,
    wherein the signal-processing means is designed to detect a variation in the ratio between the light transmission associated with the first wavelength and the light transmission associated with the second wavelength during an inspection of a plurality of eggs in succession and to correct an effect of the variation in the ratio on the decision whether or not an egg contains blood.

2. The device according to claim 1, wherein the LED emits essentially amber light, in particular in a spectrum from 550-620 nm.

3. The device according to claim 1, wherein the first wavelength is approximately 600 nm and the second wavelength is approximately 577 nm.

4. The device according to claim 1, wherein the detection means comprise a first sensor with a first filter placed in front thereof, which selectively allows to pass light of the first wavelength, and a second sensor with a second filter placed in front thereof, which selectively allows to pass light of the second wavelength.

5. The device according to claim 4, wherein the first sensor and the second sensor comprise a photodiode.

6. The device according to claim 4, wherein the first filter and the second filter comprise an interference filter.

7. The device according to claim 4, wherein the detection means comprise a semitransparent mirror, which semitransparent mirror deflects part of the light transmitted through the egg to one of the sensors and transmits part of the light to the other sensor.

8. The device according to claim 4, wherein the detection means comprise a dichromatic mirror, which dichromatic mirror acts as a mirror for the one wavelength and allows light at the other wavelength to pass through.

9. The device according to claim 1, wherein the LED is provided with a fitted optical element in order to focus the light beam onto the egg.

10. The device according to claim 1, wherein the signal-processing means comprise a microprocessor.

11. The device according to claim 1, wherein the signal-processing means comprise adjustable amplifiers for amplifying the signals originating from the detection means in such a manner that the variation in the ratio between these signals is compensated for.

12. A method for inspecting eggs for the presence of blood, in which:
    light is transmitted through an egg to be inspected by means of an LED, which light comprises a first wavelength which is not selectively absorbed by blood and comprises a second wavelength which is selectively absorbed by blood,
    the light transmission through the egg to be inspected at the two wavelengths is converted into corresponding signals, said signals each being representative of the light transmission at the wavelength concerned, based on the signals, the ratio is determined between the light transmission associated with the first wavelength and the light transmission associated with the second wavelength and it is decided on the basis of this ratio whether or not an egg contains blood, and wherein a variation in the ratio between the light transmission associated with the first wavelength and the light transmission associated with the second wavelength is detected during an inspection of a plurality of eggs in succession and an effect of the variation in the ratio on the decision whether or not an egg contains blood is corrected.

13. The method according to claim 12, wherein it is decided whether or not an egg contains blood by means of a comparison of the ratio between the light transmission for the first wavelength and the light transmission for the second wavelength and a threshold value, it being decided that an egg contains blood when the ratio exceeds the threshold value.

14. The method according to claim 13, wherein the ratio between the light transmission associated with the first wavelength and the light transmission associated with the second wavelength is monitored.

15. The method according to claim 14, wherein the ratio between the light transmission associated with the first wavelength and the light transmission associated with the second wavelength is monitored using statistically determined values of this ratio, preferably average values, which value is determined in each case for a group of a specific number of eggs.

16. The method according to claim 14, wherein, when it varies, the ratio between the light transmission associated with the first wavelength and the light transmission associated with the second wavelength is corrected in such a manner that the threshold value can be kept constant.

17. The method according to claim 14, wherein the threshold value is corrected when the ratio between the light transmission associated with the first wavelength and the light transmission associated with the second wavelength varies.

18. The method according to claim 12, wherein the LED is alternately switched on and off, a dark measurement being carried out by the device when an LED is switched off in order to carry out an offset compensation.

19. A method for inspecting eggs, using a device for inspecting eggs for the presence of blood, wherein light within a certain narrow spectrum is produced by a one or more identical LED's (Light Emitting Diode) and is passed through an egg to be inspected, which narrow spectrum comprises both a first and a second wavelength, wherein the light of the first wavelength is not selectively absorbed by blood and the light of said second wavelength is selectively absorbed by blood, light transmission through the egg to be inspected for each of the two wavelengths is converted by detection means into corresponding signals, each of the said signals being representative of the light transmission at the relevant wavelength, a ratio between the light transmission associated with the first wavelength and the light transmission associated with the second wavelength is determined by signal processing means based on the signals emanating from the detection means and a decision signal which is representative of the decision whether or not an egg contains blood on the basis of this ratio is emitted by the signal processing means, wherein the signal-processing means is designed to detect a variation in the ratio between the light transmission associated with the first wavelength and the light transmission associated with the second wavelength during an inspection of a plurality of eggs in succession and to correct an effect of the variation in the ratio on the decision whether or not an egg contains blood.

20. The device of claim 1, wherein detect the variation in the ratio between the light transmission associated with the first wavelength and the light transmission associated with the second wavelength comprises determining an average ratio value of the plurality of eggs, and detecting that the average ratio value is moving.

21. The device of claim 20, wherein correcting the effect comprises applying a correction factor to the ratio between the light transmission associated with the first wavelength and the light transmission associated with the second wavelength to compensate for a spectrum shift of the light within the certain narrow spectrum produced by a temperature change of the one or more identical LED's.

22. The method of claim 12, wherein the variation in the ratio between the light transmission associated with the first wavelength and the light transmission associated with the second wavelength is detected comprises determining an average ratio value of the plurality of eggs, and detecting that the average ratio value is moving.

23. The method of claim 22, wherein the effect of the variation is corrected comprises applying a correction factor to the ratio between the light transmission associated with the first wavelength and the light transmission associated with the second wavelength to compensate for a spectrum shift of the light within the certain narrow spectrum produced by a temperature change of the means of the LED.

24. The method of claim 19, wherein detect the variation in the ratio between the light transmission associated with the first wavelength and the light transmission associated with the second wavelength comprises determining an average ratio value of the plurality of eggs, and detecting that the average ratio value is moving.

25. The method of claim 24, wherein correct the effect comprises applying a correction factor to the ratio between the light transmission associated with the first wavelength and the light transmission associated with the second wavelength to compensate for a spectrum shift of the light within the certain narrow spectrum produced by a temperature change of the one or more identical LED's.

* * * * *